(12) United States Patent
Noras

(10) Patent No.: US 10,987,061 B2
(45) Date of Patent: Apr. 27, 2021

(54) PATIENT TABLE FOR NMR MAMMOGRAPHY

(71) Applicant: Hubert Noras, Würzburg (DE)

(72) Inventor: Hubert Noras, Würzburg (DE)

(*) Notice: Subject to any disclaimer, the term of this patent is extended or adjusted under 35 U.S.C. 154(b) by 1180 days.

(21) Appl. No.: 14/910,165

(22) PCT Filed: Nov. 27, 2014

(86) PCT No.: PCT/DE2014/100417
§ 371 (c)(1),
(2) Date: Feb. 4, 2016

(87) PCT Pub. No.: WO2015/078452
PCT Pub. Date: Jun. 4, 2015

(65) Prior Publication Data
US 2016/0256110 A1 Sep. 8, 2016

(30) Foreign Application Priority Data
Nov. 29, 2013 (DE) .................... 10 2013 113 276.6

(51) Int. Cl.
*A61B 5/00* (2006.01)
*A61B 5/055* (2006.01)
*A61B 5/05* (2021.01)

(52) U.S. Cl.
CPC ............ *A61B 5/708* (2013.01); *A61B 5/0555* (2013.01); *A61B 5/4312* (2013.01); *A61B 5/05* (2013.01); *A61B 5/055* (2013.01)

(58) Field of Classification Search
None
See application file for complete search history.

(56) References Cited

U.S. PATENT DOCUMENTS

| 2005/0228267 | A1 | 10/2005 | Bulkes et al. | |
| 2007/0016003 | A1* | 1/2007 | Piron | A61B 5/415 600/415 |
| 2007/0223652 | A1 | 9/2007 | Galkin | |
| 2007/0250047 | A1 | 10/2007 | Harter | |
| 2009/0054757 | A1* | 2/2009 | Noras | A61B 6/502 600/415 |

(Continued)

FOREIGN PATENT DOCUMENTS

| DE | 202006004127 U1 | 8/2006 |
| DE | 102007006855 A1 | 8/2008 |

(Continued)

*Primary Examiner* — Katherine L Fernandez
*Assistant Examiner* — Michael S Kellogg
(74) *Attorney, Agent, or Firm* — Franco S. DeLiguori; DP IP Group

(57) ABSTRACT

There is disclosed a patient table for NMR mammography comprising a test subject for and two openings with are intended for inserting a breast in each case, coils being present in the immediate vicinity thereof, characterised in that in the region of an opening, below the table, a band (3) is attached, which is guided medially inwardly from the outside of the table or of the test subject, here surrounds the breast cranially or caudally, and then runs from the medial side, bearing against the breast for caudal or cranial contact with the breast, the ends of the band (13) being guided laterally outwardly, where they run adjacent to one another.

2 Claims, 2 Drawing Sheets

(56) References Cited

U.S. PATENT DOCUMENTS

2010/0004529 A1* 1/2010 Henke-Sarmento ... A61B 5/055
                                                    600/422
2010/0128843 A1* 5/2010 Tita ..................... A61B 6/0414
                                                    378/37
2011/0129062 A1* 6/2011 Hoernig ............... A61B 6/0421
                                                    378/37

FOREIGN PATENT DOCUMENTS

DE   102009056176 A1   6/2011
EP        2964087 B1   11/2014
WO      2015078452 A1   6/2015

* cited by examiner

PATIENT TABLE FOR NMR MAMMOGRAPHY

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This patent claims priority from International PCT Patent Application No. PCT/DE2014/100417, Nov. 27, 2014 entitled, "PATIENT SUPPORT FOR NMR MAMMOGRAPHY", which claims priority to German Patent Application No. 10 2013 113 276.6, filed Nov. 29, 2013 entitled, "PATIENT SUPPORT FOR NMR MAMMOGRAPHY", all of which are incorporated herein by reference in their entirety.

BACKGROUND

The invention relates to a patient table for NMR mammography comprising a test subject for and two openings with are intended for inserting a breast in each case, coils being present in the immediate vicinity thereof.

The mammary carcinoma, as one of the most dangerous malignant tumours, is one of the most frequent causes of death of women due to its wide incidence. Greatest importance is therefore attached to preventive examinations for early detection. As imaging examination processes, X-rays are used in X-ray mammography, in other examination procedures ultrasound (sonography) and, recently, nuclear spin tomography processes are more often used. In the latter case, it has been found that the sensitivity, that is to say the sensitiveness of the detection of cancerous tissue, is higher than in the case of investigation with X-rays or ultrasound. The investigation principal consists essentially in the fact that protons in a constant magnetic field obtain an external energy supply due to an alternating electromagnetic field, which leads to an excitation of the spin energy. With relaxation, that is to say after the return to its initial state, a radio wave is emitted from the spin, which can be registered by means of suitable detectors. The greater the number of protons, as occur, in particular, to an elevated extent in water-containing tissue, the higher is the signal density that is emitted and measured. Anatomic anomalies can be thereby diagnosed and assessed. For breast examinations, contrast agents are applied, which accumulate to a particular degree at places where an elevated blood flow predominates, and which lead to a substantial improvement of the imaging quality and its meaningfulness. The further development and improvement of such devices for mammography are an object of the subsequent invention.

NMR mammography is performed in such a manner that the patient is caused to lie face down on a patient table, where the breasts are in each case threaded into an opening and examined below the table. For this purpose, in the direct vicinity of the tissue to be investigated, the receiver coils for the emitted radio waves are attached.

The present invention has taken the development of this device for mammography as its object and aims to allow the examination to be performed in the shortest time possible and to obtain an optimum image quality.

This object is achieved according to the invention in that, in the region of an opening, below the table, a band is attached, which is guided medially inwardly from the outside of the table or of the test subject, here surrounds the breast cranially or caudally, and then runs from the medial side, bearing against the breast for caudal or cranial contact with the breast, the ends of the band being guided laterally outwardly, where they run adjacent to one another.

The fundamentals of the proposals according to the invention consist in the finding that a fixing of the breast on all sides ensures that there is no relative movement of the measurement object during the time of the imaging, and consequent fuzziness, and at the same time that the number of layers to be imaged, irrespective of whether they extend in the transverse or sagittal direction, are minimized because of the compression of the breast. The smaller the number of layers to be recorded for imaging the entire object, the faster the imaging can be performed. If the tissue region to be received is greatly reduced in its dimensions, the imaging can be performed faster than would be the case with the imaging of breasts of larger dimensions.

The proposed solution consists in using a band, which is guided medially inwardly from the outside of the table or of the test subject, here surrounds the breast cranially or caudally, and then runs from the medial side, bearing against the breast for caudal or cranial contact with the breast. The band is then guided laterally outwardly and then ends on or in the vicinity of the starting point of the band. The fixing with the aid of the band takes place in that the band is tensioned in the axial direction and is then tensioned in the axial direction outwardly in the lateral direction with respect to the plane of the body, and compression of the breast on all sides thereby takes place. The band forms a virtually closed loop, which is laid around the breast and drawn together to fix it. In practice, it is unimportant whether both ends of the band undergo tensile loading in the axial direction or whether one end is fixed and only the other end is subject to tension. The tension compresses the breast around the entire circumference and inwardly in a radial direction and leads to a fixing for the duration of the NMR imaging. The fixing is conducted by a single continuous tension in the axial direction at the end of the band.

Within the scope of the invention, it is inconsequential in what manner the tensile forces are exerted, that is to say whether it is a manual or motor-driven tensioning operation. A further substantial advantage can also be seen in the fact that, in the fixed state, tissue samples can be taken by puncturing the bands with a biopsy needle. The fixed state permits a particularly precise and targeted removal of the respective tissue.

For the concrete constructional design and implementation of the concept according to the invention, there are various possibilities within the scope of the invention. Particularly preferred is a solution in which a pressure block is used which is disposed in a lateral direction outside the breast and which serves for the reception of the outgoing and also of the returned band at its ends. To this end, two slits running approximately perpendicular to the body plane are provided at a distance from one another, which serve for the threading in of the two ends of the band, the ends projecting outwardly. In the medial direction, starting from the pressure block, specifically essentially concentric to the breast opening, the bands form a sling in such a manner that on guiding in of the breast there is first a spacing between the breast and band. If a tension is now exerted in the axial direction at one or both of the ends, specifically from laterally outside the pressure block, this leads to the loop being pulled together and the breast itself being completely encircled, even with the inclusion of the pressure block. The axial tension is continued until a resistance indicates the area contact with the breast tissue and the desired compression has built up. In principle, it is conceivable for not only the belt to be axially tensioned, but also for the pressure block to be additionally displaced in the medial direction. The result is that, with a single tensioning movement and therefore very rapidly, a fixing of the breast at all sides can be performed in a very short time.

For the guiding of the band, in expedient embodiments, various measures are conceivable. After the band in the starting position must release the opening for threading in the breast, otherwise the introduction would be prevented or at least made difficult, it is advisable to temporarily outwardly secure the belt in the edge region of the opening or in the radial direction. For this purpose, the band has on its outer surface a hook-and-loop fastener, which cooperates with the corresponding counter surface. If tension is then exerted on the band in the axial direction, the hook-and-loop fastener is released and the band can be moved towards the centre point of the opening, that is to say towards the centre of the breast, and the desired fixing can be thereby performed.

A further possibility consists in the fact that the pressure block is located opposite a bridge, through which the band was threaded. By this measure, the opening is first kept clear by the band, so that the threading in of the breast is also made easier here and, under tension, the band that is fixed on the bridge will then move the pressure block towards the bridge and in this manner transform to the fixing position.

In a constructional alternative of great importance, it is proposed to lead the band in the form of a polygon, in particular of a rectangle, in a plane that is also parallel to the plane of the body, and at the corner points to apply a deflector roller in each case, which cause the bands to describe an angle of 90 degrees and more, and are assigned to the two pressure rollers, which ensure that the band, both incoming and outgoing, is pressed on the deflector roller by the pressure roller in the direction of the (local) anglebisector, and thus, as a result, moves the pressure rollers approximately towards one another. The pressure rollers ensure that the band remains in body contact over the entire circumference and the deflector roller itself remains spaced so that no contact can occur. The pressure rollers have the consequence that the band is guided over the entire circumference of the deflector roller. The adaptation and fixing of the breast is performed in such a manner that the corner points consisting of the two pressure rollers and the deflector roller can be traversed via a slide in two directions, for example with the aid of cross slides in the manner of a Cartesian coordinate system, and can be moved towards one another to the extent that the band comes into contact with the breast on all sides. The movement of the corner points is solved in that a tension is exerted on the band in the axial direction so that the corner points are "pulled together" against a restoring force. With this constructional solution, too, it is unimportant whether one end of the belt is spatially fixed and only the other end can be tensioned or whether both ends of the belt, which then come to lie directly against one another, are tensile-loaded simultaneously or independently of one another.

With this device, too, a rapid fixing of the breast, with the desired advantages, is then obtained.

In an expedient embodiment, it is proposed, both in the fixing unit and/or in the bands, to fit coils, which can be medially or laterally pushed in or plugged in In the case of the bands themselves, they may be sterile products that permit tissue samples to be taken. It is also conceivable that a mesh with openings, known as a "grid" in technical language, can be introduced into the bands.

The considerations until now have been limited to achieving a compression and fixing of the breast in a plane parallel to the plane of the body. In a further embodiment, it is therefore advisable to cause the coil to approach and press on from below, that is to say perpendicular to this plane, and therefore towards the nipple, in order to achieve a compression and the desired minimization of the breast volume to be examined from this side, too. By means of the fixing element, which is equipped with coils, a movement perpendicular to the above-described plane takes place, so that, as a result, a three-dimensional fixing of the breast is obtained. By means of the further coil, a considerable improvement of the image quality is additionally obtained.

For the test subjects, it is often experienced as unpleasant that the body weight is supported on the substrate almost entirely via the breast bone (sternum). It is therefore advisable to mount supports such that they can be upwardly traversed in a direction perpendicular to the patient table and outside the sternum and to support the body thereby. In this manner, a distribution of the flow of forces and a reduction of the spot pressure loading are achieved, which the test subject experiences as pleasant.

DESCRIPTION OF THE DRAWINGS

Further details and features of the invention are explained in the descriptive part below in greater detail with reference to an example. In schematic view.

DETAILED DESCRIPTION

Figure 1:
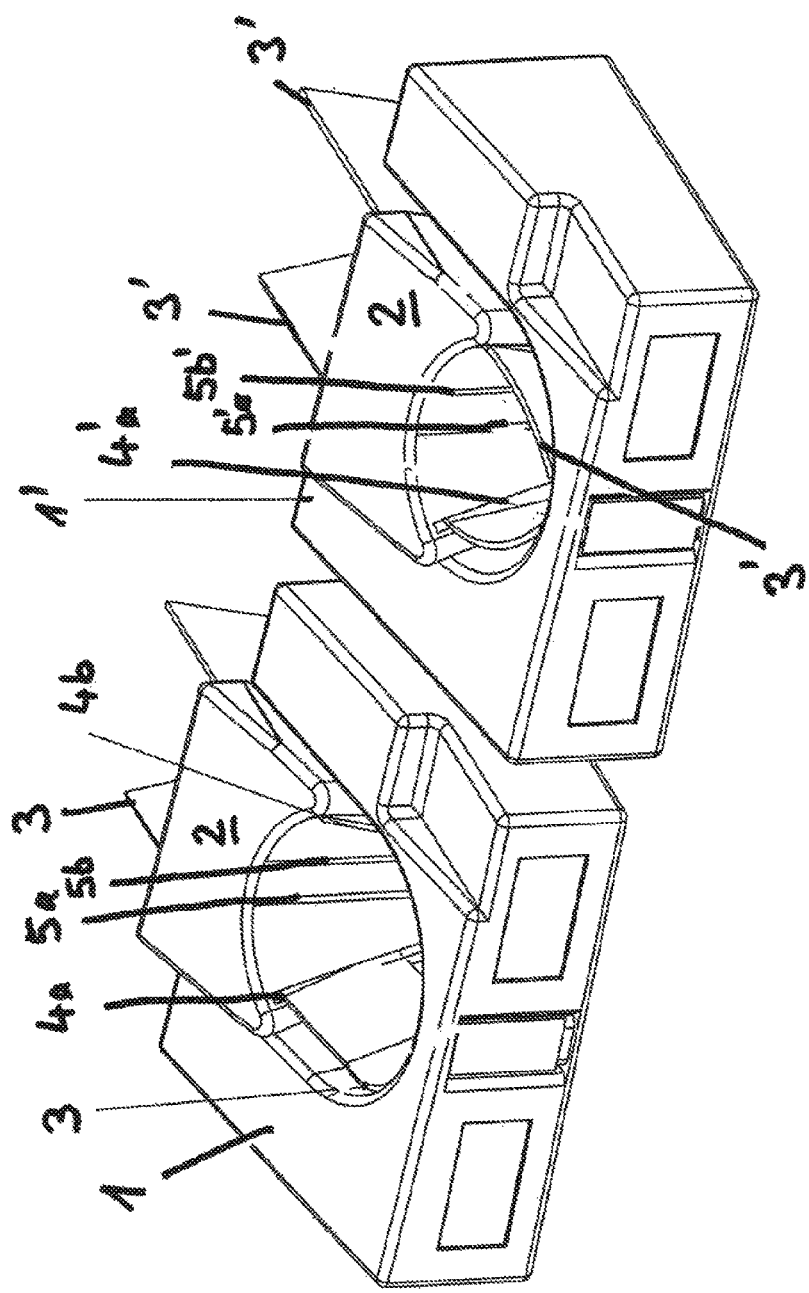
FIG. 1 shows the fixing device with a pressure block

FIG. 1 shows a pressure block 2, which is mounted so as to be displaceable in a fixing device 1, which, in turn, is integrated below the patient in a patient table (which is not shown). For the sake of clarification, in the schematic diagram, only the fixing device 1 is shown, wherein by immediate comparison of the two different positions, which are shown side by side, of two fixing devices 1, the recognition of the kinematic relationships is made clear. The left-hand fixing device 1 shows that phase in which one breast has not yet been introduced, while the right-hand fixing device 1', shows that in which the breast (which is also not shown) is fixed. The pressure block 2 is fixed, so as to be displaceable relative to the fixing device 1, in the plane of the latter, the displacement direction in the installed state taking place in the medial direction (or laterally during opening). The fixing device 1 describes a groove emerging from the edge of the fixing device 1, which, in the edge region, is closed via the pressure block 2, the shape of this groove and the end face of the pressure block 2 being shaped such that an essentially circular and through-going opening remains. In this opening, the breast is subsequently introduced with its centre axis perpendicular to the surface of the fixing device, and thus also perpendicular the plane of the patient's body. For fixing, the band 3 is used, which emerges from the outer surface of the pressure block 2, passes through a corresponding slit 4 and emerges from the pressure block 2 on the inner side, and is subsequently guided thereon approximately in the form of a semicircle, and then passes back to the pressure block 2, where the band 3 is guided outwardly via a further slit 4'. Therein, the band runs essentially mirror-symmetrically to a centre plane, which is oriented approximately parallel to the profile of the band 3. The two ends of the band 3 project outwardly in order to permit access to the end of the band 3 and to be able to exert an axial tension on the band 3. In the region of the semicircle, the band 3 is guided along the inner surface of the fixing device 1. A detachable fastening of the band 3, which is not shown, ensures that the entire cross-section is kept clear, so that the threading through of the breast is made easy. The pressure block 2 shows, on its inner surface, adjacent to the slits 4 and 4', approximately in the centre plane, two further slits 5, 5', which run parallel to one another, and which open up the possibility of being able to thread in the ends of the band 3 there instead of into the slits 4, 4'. The result is then a constriction of the clear width described by the fixing device 1 and pressure block 2, which itself shortens the phase of threading in and fixing.

In the device 1' shown at the right next to that just described, the phase is shown in which the breast (not shown) is fixed. A description of the individual parts has already been given in relation to the left-hand illustration, and can be omitted to avoid repetition. The reference characters shown in the right-hand figure correspond to those of the left-hand illustration; however they have been shown with an apostrophe for the sake of differentiation.

However, the difference consists in the fact that the pressure block 2 is displaced inwardly, which succeeds in that an axial tension is exerted on one or both ends of the band 3. By this means, the connection of the band 3 is at least partly solved with the end face that runs in the opening The loop formed by the band 3 is drawn together until there is all-round contact with the breast by the band 3 and the pressure block 2. The fixing of the breast is thus ended and the creation of images can begin.

Figure 2:
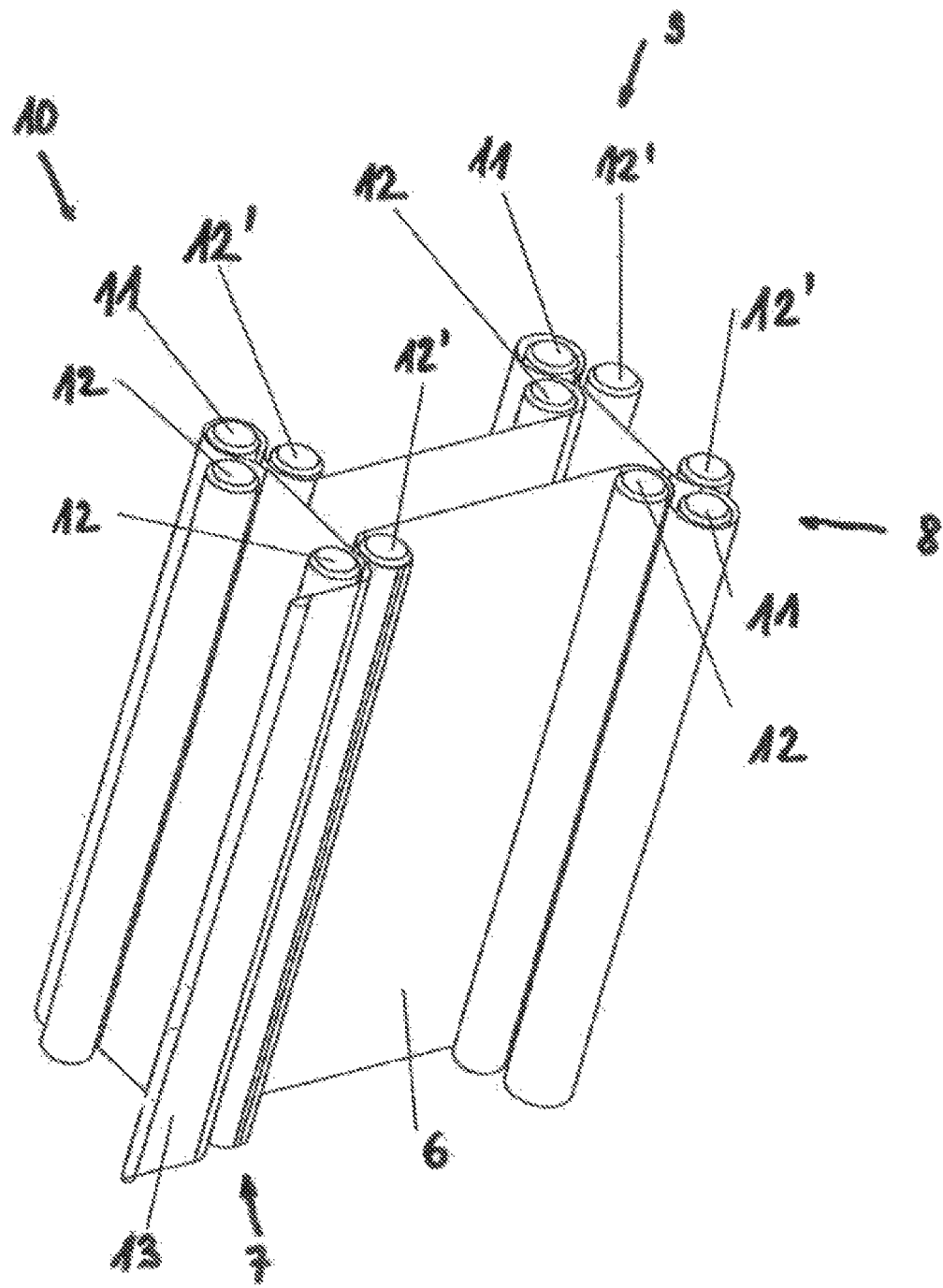
FIG. 2 shows a fixing device with a band, which is guided in the form of a rectangle

FIG. 2 shows an alternative realization of the fixing device according to the invention. In the illustration shown there, the band 6 is guided between four corner points 7, 8, 9 and 10 such that the band 6, in top view, that is to say when viewed in the plane of the band 6, describes a rectangle in principle. Those surfaces of the band 6 that lie opposite one another are thereby oriented parallel to one another. With the exception of the corner point 7, the corner points 8-10 are of the same construction in principle, that is to say they consist of a deflector roller 11 and two pressure rollers 12 in each case. The guidance takes place in such a manner that the deflector rollers 11 are mounted at the corner points and the band 6 fed to the deflector roller 11 is pressed by means of one of the two pressure rollers 12 and the band 6 guided away is also pressed via the second pressure roller 12', specifically in such a manner that the band 6 almost completely encircles the deflector roller 11. Each of the two pressure rollers 12 (or 12' in each case) presses the band 6 towards the opposite-laying pressure roller 12' (or 12 in each case). That region of the band 6 that is located between the corner point 7-10, more accurately between their pressure rollers 12, 12', is used for fixing the breast.

Of the corner points 8-10, corner point 7 differs in that, instead of the deflector roller, the band 6 is guided with at least that one end, and opens up the possibility of exerting tension on the band 6 in an axial direction. The opposite end of the band 6 is fixed on the pressure roller 12 that belongs to this deflector roller 11.

In the drawing, it is not identifiable that the arrangement forming the corner points 7-10 can be traversed against a restoring force in a plane perpendicular to the band 6. With a rectangular guidance of the band 6, as shown, cross-slits can be used for this purpose.

The use takes place in such a manner that the corner points 7-10 are moved apart until the breast to be examined can be threaded through between the rectangle formed from the bands 6. Subsequently, by tension on the end 13 of the band 6, a force is exerted, which has the effect that all corner points 7-10 are moved towards one another so that the breast undergoes a constriction and a corresponding counterforce builds up. In this manner, the breast is permanently fixed and the images can be made.

The illustrated exemplary embodiments have the common feature that a band 3 is used which encircles the breast in a loop and fixing takes place in an axial direction when they are drawn together.

LIST OF REFERENCE CHARACTERS

1 Fixing device
2 Pressure block
3 Band
4a, 4b (outer) slit
5a, 5b (inner) slit
6 Band
7-10 Corner point
11 Deflector roller
12, 12' Pressure roller
13 Band end It is claimed:

1. A patient table for performing NMR mammography on a patient, comprising: a table for supporting a patient in a face-down position, the table having an upper surface and an underside, the table defining a plane and having at least one opening for inserting a breast of the patient; a band attached to the underside of the table in a region of the at least one opening, the band being configured to be laid around the breast so as to surround and contact the breast on at least three sides including a cranial, a caudal and a medial side of the breast; and a pressure block configured to be disposed in a lateral direction outside of the breast and in contact with a lateral side of the breast, the pressure block being moveable relative to the table and being configured to receive a first end portion and a second end portion of the band, and the pressure block being movable towards and located opposite a bridge through which the band is threaded.

2. A patient table for performing NMR mammography on a patient, comprising: a table for supporting the patient in a face-down position, the table having an upper surface and an underside, the table defining a plane and having at least one opening for inserting a breast of the patient; and a band attached to the underside of the table in a region of the at least one opening, the band being configured to be laid around the breast so as to surround and contact the breast on at least three sides including a cranial, a caudal and a medial side of the breast; wherein in a plane that is parallel to the plane of the table, the band describes a course of the shape of a polygon having three or more corner points; wherein at each corner point of the polygon, with the exception of a first corner point, a deflector roller is mounted, each deflector roller being encircled by the band and having two co-located pressure rollers which press an infed part and an outgoing part of the band at that corner point against the deflector roller; wherein each of the deflector rollers and its two co-located pressure rollers are traversable, against a restoring force, via a slide in two linearly independent directions; and wherein the first corner point of the polygon has only two pressure rollers which guide the band laterally outward.

\* \* \* \* \*